United States Patent [19]

Schlesinger et al.

[11] Patent Number: 5,104,854
[45] Date of Patent: Apr. 14, 1992

[54] ANTIVIRAL PEPTIDES

[75] Inventors: Milton J. Schlesinger; Nancy C. Collier, both of St. Louis; Steven P. Adams, St. Charles, all of Mo.

[73] Assignee: Washington University, St. Louis, Mo.

[21] Appl. No.: 703,422

[22] Filed: May 21, 1991

Related U.S. Application Data

[63] Continuation-in-part of Ser. No. 305,148, Feb. 1, 1989, Pat. No. 5,026,686.

[51] Int. Cl.$^5$ .................. A61K 37/02; C07K 7/06
[52] U.S. Cl. ................................ 514/15; 530/328
[58] Field of Search .................. 530/324–328; 514/12–15

[56] References Cited

U.S. PATENT DOCUMENTS 5,026,686  6/1991  Schlesinger et al. ................ 514/14

OTHER PUBLICATIONS

Cohen, Science 205, 964–971 (1979).
Dolin, Science 227, 1296–1301 (1985).
Robins, Chem. & Eng. News 64, 28–40 (1986).
Hirsch & Kaplan, Scient. Amer. 256(4), 76–85 (1987).
Varmus, Science 240, 1427–1435 (1988).
Strauss et al., Virology 132, 92–110 (1984).
Schlesinger & Schlesinger, The Togaviridae and Flaviviridae, Plenium Press, N.Y. 1986, pp. 35–43.
Schlesinger & Cahill, Virology, 168, 187–190 (1989).
Hiti et al., Virology, 111, pp. 113–124 (1981).

*Primary Examiner*—Lester L. Lee
*Attorney, Agent, or Firm*—Scott J. Meyer; Paul L. Passley

[57] ABSTRACT

Novel antiviral peptides are disclosed which have a sequence of about 6 to 30 amino acids and which are substantially identical to a small portion of a glycoprotein in a virus that contains a lipid-bilayer in its structure. A preferred peptide having antiviral activity against influenza virus is the decapeptide amide N-G-S-L-Q-C-R-I-C-I-NH$_2$ [SEQ ID NO:3].

2 Claims, 3 Drawing Sheets

ANTIVIRAL PEPTIDES

CROSS-REFERENCE TO RELATED APPLICATION

This is a continuation-in-part of copending application Ser. No. 07/305,148, filed Feb. 1, 1989 now U.S. Pat. No. 5,026,686.

BACKGROUND OF THE INVENTION

This invention relates to novel antiviral peptides and, more particularly, to small peptides which interfere with the final stages of virus intracellular replication.

Although powerful chemotherapeutic agents have been developed for successful treatment of bacterial infections, e.g. the penicillins and cephalosporins, no such comparable antiviral therapies have been devised. Despite the vast number of compounds screened in the past several decades and the multi-millions of dollars spent on development, only a handful of drugs have had limited clinical utility in controlling viral infections. Among the types of compounds having been found to have limited success, the following are illustrative:

Aminoquinolines, e.g. chloroquin (U.S. Pat. No. 2,233,970);
Amantadine (U.S. Pat. No. 3,310,469);
Phosphonoacetic acid or PAA (U.S. Pat. No. 3,767,795);
Phosphonoformic acid (U.S. Pat. 4,771,041);
Purine and pyrimidine nucleosides, e.g. 9-β-D-arabinofuranosyladenine (vidarabine or ara-A, U.S. Pat. No. 3,616,208);
AraH$_x$MP (U.S. Pat. No. 4,093,714);
2'-Deoxy-5-iodouridine (idoxuridine or IDU) and derivatives (U.S. Pat. No. 4,000,260);
Ribavirin (U.S. Pat. No. 3,798,209);
Acyclovir and derivatives (U.S. Pat. No. 4,199,574);
3'-Azido-3'-deoxythymidine (azidothymidine or AZT) (U.S. Pat. No. 4,724,233).

A significant problem that exists with the analogs of pyrimidines and purines is that they are most often as toxic to an uninfected cell as to virus multiplication in that cell.

Any attempt to treat a viral infection must take into account the various methods by which the virus interacts with the host cell. Viruses consist of a shell of protein enclosing a core of nucleic acid, either ribonucleic acid (RNA) or deoxyribonucleic acid (DNA), that codes for viral reproduction. That is, the RNA or DNA is the genetic material which carries the genes specifying the enzymes and structural proteins that the virus needs to interact with the host cell and reproduce itself. This protein shell also serves as a protective coat to keep the nucleic acid intact and prevent enzymic destruction. Some viruses also contain, in addition to their protein coat, an outer covering referred to as an envelope. This envelope consists of a lipid bilayer which is derived from membranes of the cell in which the virus has replicated and glycoproteins whose sequences are encoded in the virus genome. The structure of these glycoproteins consists of an outer, extra-cellular domain, a transmembranal domain and a cytoplasmic domain which is localized to the interior of the lipid bilayer. Current antiviral therapy thus has attempted to exploit the subtle molecular contrasts between virus and host and to develop antiviral compounds that will interfere with biochemically defined virus-specific functions. See, for example, Cohen, Science 205, 964-971 (1979); Dolin, Science 227, 1296-1303 (1985); Robins, Chem. & Eng. News 64, 28-40 (1986); Hirsch and Kaplan, Scientific Amer. 256(4), 76-85 (1987); and Varmus, Science 240, 1427-1435 (1988).

BRIEF DESCRIPTION OF THE INVENTION

The present invention relates to small novel antiviral peptides which interfere with the final stages of virus intracellular replication. These novel peptides contain sequences preferably of about 6 to 30 amino acids which are substantially identical to a small portion of a viral glycoprotein in those viruses that contain a lipid-bilayer in their structure.

The cytoplasmic domain of the glycoprotein is recognized by the virus intracellular nucleocapsid or matrix protein, and a binding of the latter to the glycoprotein occurs during the final assembly of the virus. Extracellular virions must contain lipid and embedded glycoproteins in order to reinfect other cells in an organism and cause disease. The sequences of the small peptide inhibitors of this invention are unique in that they have sequences substantially identical to a domain in the glycoprotein which participates in binding. They should not have an effect on uninfected host cells.

In an illustrative embodiment of the invention, the antiviral peptide is identical to a small portion of the cytoplasmic domain of Sindbis E2 glycoprotein and preferably is a hexapeptide with the sequence L-T-P-Y-A-L [SEQ ID NO:1]or a heptapeptide with the sequence L-T-P-Y-A-L-A [SEQ ID NO:2]or their carboxamide derivatives.

In accordance with another embodiment of the invention, the foregoing novel peptides containing unique sequences of about 6 to 30 amino acids which are substantially identical to a small portion of the viral cytoplasmic domain can be provided with enhanced antiviral activity by modifying the N-terminus with an acyl group having from 2 to about 12 carbon atoms, preferably octanoyl.

In another preferred embodiment of the invention, addition of an octanoyl group to the amino-terminal leucine of a Sindbis virus inhibitory peptide, L-T-P-Y-A-L-A [SEQ ID NO:2], increased the inhibitory potency 10 fold. When tested on tissue culture cells, this peptide was specific for two alphaviruses, Sindbis and Semliki Forest. It had no effect on uninfected cells or on cells infected with two non-alphaviruses, viz. a rhabdovirus (vescular stomatitis virus) and an orthomyxo virus (influenza).

In still other embodiments of the invention, the antiviral peptides are identical to small portions of the glycoproteins of influenza virus and vesicular stomatitis virus (VSV). These antiviral peptides can be identical to small portions of the HA2-cytoplasmic domain of influenza virus and the G-cytoplasmic domain of vesicular stomatitis virus. A preferred example of the influenza virus inhibitory peptide is a decapeptide amide with the sequence N-G-S-L-Q-C-R-I-C-I-NH$_2$ [SEQ ID NO:3]-that corresponds to residues 213-222 at the carboxy terminus of the HA2 of A/WSN strain of influenza virus. A preferred example of the vesicular stomatitis virus inhibitory peptide is a 29 residue peptide with the sequence R-V-G-I-H-L-C-I-K-L-K-H-T-K-K-R-Q-I-Y-T-D-I-E-M-N-R-L-G-K [SEQ ID NO:4]that corresponds to residues 483-511 of the G protein of VSG (Indiana).

It should be understood that variations in the individual amino acids of the peptides or in their end groups which do not adversely or detrimentally affect the desired biological activity as defined herein are included within the scope of the invention. For example, conversion of the peptides into the peptide amide form is a useful variation for antiviral activity. A striking example of this is with the influenza peptides; the same peptide with a carboxyl group at the terminus is inactive whereas an amide group at the carboxy-terminus produces an inhibitory structure.

DETAILED DESCRIPTION OF THE INVENTION

While the specification concludes with claims particularly pointing out and specifically claiming the subject matter regarded as forming the present invention, it is believed that the invention will be better understood from the following detailed description of preferred embodiments taken in conjunction with the accompanying drawing in which:

Figure 1:
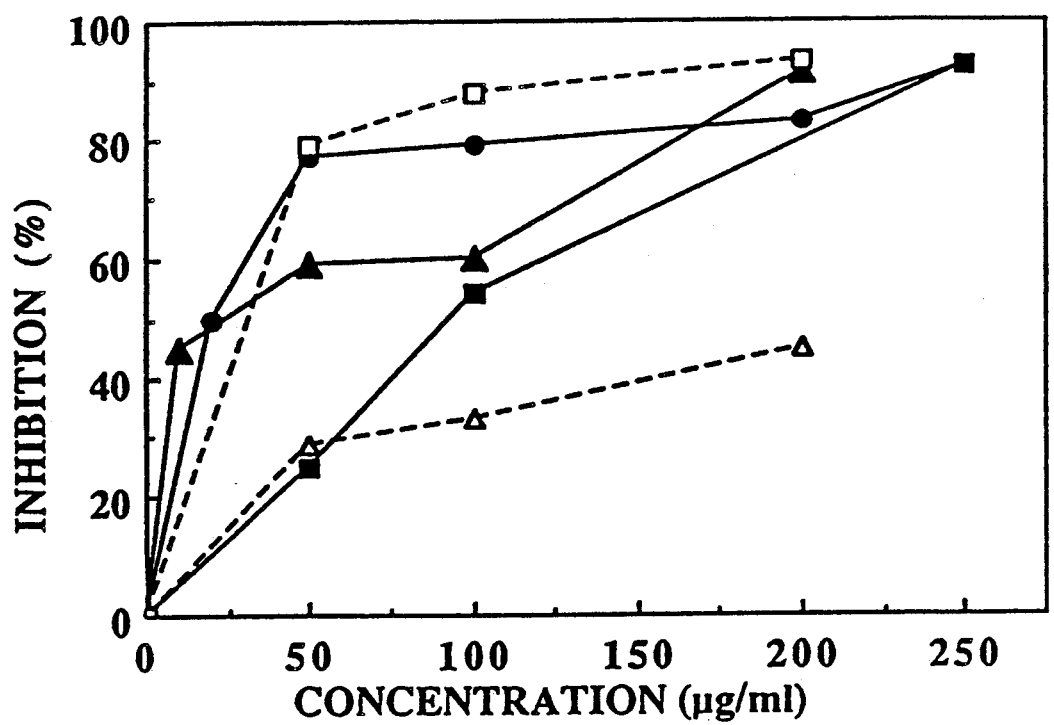
FIG. 1 is a graphical representation which shows the dose-dependent inhibition of influenza virus formation by the peptide HA2(213–222), NGSLQCRICI-amide [SEQ ID NO:3].

The novel antiviral peptides of this invention can be prepared by known solution and solid phase peptide synthesis methods.

In conventional solution phase peptide synthesis, the peptide chain can be prepared by a series of coupling reactions in which the constituent amino acids are added to the growing peptide chain in the desired sequence. The use of various N-protecting groups, e.g., the carbobenzyloxy group or the t-butyloxycarbonyl group (BOC), various coupling reagents, e.g., dicyclohexylcarbodiimide or carbonyldimidazole, various active esters, e.g., esters of N-hydroxyphthalimide or N-hydroxy-succinimide, and the various cleavage reagents, e.g., trifluoroacetic acid (TFA), HCl in dioxane, boron tris-(trifluoracetate) and cyanogen bromide, and reaction in solution with isolation and purification of intermediates is well-known classical peptide methodology.

The preferred peptide synthesis method follows conventional Merrifield solid-phase procedures. See Merrifield, *J. Amer. Chem. Soc.* 85, 2149–54 (1963) and *Science* 150, 178–85 (1965). This procedure, though using many of the same chemical reactions and blocking groups of classical peptide synthesis, provides a growing peptide chain anchored by its carboxy terminus to a solid support, usually cross-linked polystyrene, styrenedivinylbenzene copolymer or, preferably, p-methylbenzhydrylamine polymer for synthesizing peptide amides. This method conveniently simplifies the number of procedural manipulations since removal of the excess reagents at each step is effected simply by washing the polymer.

The acyl group on the N-terminus is conveniently introduced by reaction of an alkanoic anhydride with the peptide on the solid support after deprotection with TFA.

Further backgroup information on the established solid phase synthesis procedure can be had by reference to the treatise by Stewart and Young, "Solid Phase Peptide Synthesis," W. H. Freeman & Co., San Francisco, 1969, and the review chapter by Merrifield in *Advances in Enzymology* 32, pp. 221–296, F. F. Nold, Ed., Interscience Publishers, New York, 1969; and Erickson and Merrifield, *The Proteins*, Vol. 2, p. 255 et seq. (ed. Neurath and Hill), Academic Press, New York, 1976.

The invention is generally applicable to those viruses having so-called envelopes or lipid-bilayers in their structure. Most such viruses are RNA viruses and are exemplified by the alphaviruses in the family Togaviridae such as Sindbis virus and Semiliki Forest virus, rubella; retroviruses such as the human immunodeficiency virus (HIV) and human T-cell leukemia virus (HTLV); influenza viruses; respiratory synctial viruses; rabies virus; and flaviviruses such as dengue virus and yellow fever virus. Examples of enveloped DNA viruses are the herpes viruses.

The following examples will illustrate the invention in greater detail although it will be understood that the invention is not limited to these specific examples.

EXAMPLE 1

In order to illustrate a preferred embodiment of the invention in greater detail, a group of small peptides were synthesized by conventional solid phase methods such as to be substantially identical to small portions of the cytoplasmic domain of the Sindbis E2 glycoprotein. The complete nucleotide sequence of the genomic RNA of Sindbis virus and the derived amino acid sequence of E2 are disclosed by Strauss et al., *Virology* 132, 92–110 (1984), and in Chapter 3, by E. Strauss and J. Strauss, of the text by S. Schlesinger and M. Schlesinger, *The Togaviridae and Flaviriridae*, Plenum Press, New York and London, 1986. The E2 glycoprotein is 423 amino acids long. E2 is formed from a polyprotein; its sequence is found in amino acids 329–751 of the polyprotein in which the first methionine is designated +1.

The cytoplasmic domain of the E2 glycoprotein is a 33 amino acid peptide stretch comprising the C-terminal amino acids 391–423 (corresponding to 719–751 in the aforesaid polyprotein). The cytoplasmic domain of the Sindbis E2 glycoprotein thus has the following amino acid sequence [SEQ ID NO:6], reading from the amino terminus to the carboxy terminus:

```
391                          400
K—A—R—R—E—C—L—T—P—Y—A—L—A—P—

410
N—A—V—I—P—T—S—L—A—L—L—C—C—V—

420
R—S—A—N—A
```

Various peptides corresponding identically to small portions of the foregoing cytoplasmic domain were synthesized in the peptide amide form by standard solid-phase peptide synthesis. The synthesized peptides were then tested as inhibitors of Sindbis virus replication (or Semliki virus in one test) in chicken embryo fibroblasts by the method described by Schlesinger and Cahill, *Virology* 168, 187-190 (1989). According to this method, replication of the virus in the presence and absence of the test peptide was measured by quantitating both the release of radio-active particles into the tissue culture medium and the amounts of radioactive virus nucleocapsids and glycoproteins remaining inside the infected cells. The test peptide at a final concentration of 1.0 mg/ml was added 3 hours post infection. Virus release was measured by isolating particles from the media of infected and [$^{35}$S]methionine-labeled chicken embryo fibroblasts and determining the amounts of [$^{35}$S]methionine incorporated into virus-specific proteins separated by sodium dodecylsulfate polyacrylamide gel electrophoresis (SDS-PAGE). The ratio of extracellular virus to intracellular virus proteins was calculated and expressed in percentages to represent the degree of inhibition.

In accordance with the foregoing assay, the most effective peptide was a hexapeptide amide of the following amino acid sequence [SEQ ID NO:7]:

L-T-P-Y-A-L.

This peptide corresponds to amino acids 397-402 in the E2 glycoprotein of the Sindbis virus. This hexapeptide is also present in the E2 glycoprotein of Eastern equine encephalitise virus [Chang and Trent, *J. Gen. Virol.* 68, 2129 (1987)] and Ross river virus [Dalgarno et al., *Virology* 129, 170 (1983)].

Other peptides corresponding to portions of the Sindbis E2 glycoprotein have been synthesized in the peptide amide form with amino acid sequences as follows:

L-T-P-Y-A-L-A.

The otanoyl group on the N-terminal leucine of the heptapeptide was introduced by reaction of octanoic anhydride with the peptide on the solid support that had been deprotected with TFA. Confirmation of the structure of the purified octanoyl heptapeptide was made by mass spectrometry. The antiviral results with the foregoing hexapeptide amide and the octanoylated heptapeptide amide are set forth in Table I and II, respectively. In Test 3 of Table I, the test virus was Semliki Forest virus; whereas, Sindbis virus was used in replicate Tests 1 and 2 of Table I and Replicate Tests 1, 2 and 3 of Table II.

TABLE I

| INHIBITION OF SINDBIS VIRUS RELEASE BY HEXAPEPTIDE L-T-P-Y-A-L$^a$ | | | |
|---|---|---|---|
| Test | | Ratio of Extracellular Virus to Intracellular Virus Proteins | |
| 1. | Peptide | .15 | (70%)$^b$ |
|  | None | .25 | |
| 2. | Peptide | .08 | (50%) |
|  | None | .16 | |
| 3. | Peptide | .20 | (36%)$^c$ |
|  | None | .31 | |

$^a$Peptide (1.0 mg/ml final level) was added 4 hr post infection with [$^{35}$S]methionine. Virus and cells were collected 2 hr. later.
$^b$Degree of Inhibition
$^c$Semliki Forest Virus Inhibition in Test 3.
Note:
1. There was no inhibition of intracellular virus protein synthesis by the peptide at this level.
2. There was no inhibition of vesicular stomatitis virus formation and secretion by the peptide at this level.

TABLE II

INHIBITION OF SINDBIS VIRUS RELEASE BY

K—A—R—R—E—C—L—T—P—Y—A—L—A—P—N—A—V—I—P—T—S—L—A*   [SEQ ID NO: 8]

R—E—C—L—T—P—Y—A—L—A—P—N—A—V—I—P—T—S—L—A*   [SEQ ID NO: 9]

K—A—R—R—E—C—L—T—P*   [SEQ ID NO: 10]

K—A—R—R—E—C   [SEQ ID NO: 11]

A—L—A—P—N—A   [SEQ ID NO: 12]

V—I—P—T—S—L   [SEQ ID NO: 13]

Y—A—L—A—P—N—A—V—I—P—T—S—L—A—L—L   [SEQ ID NO: 14]

N—A—V—I—P—T—S—L—A—L—L   [SEQ ID NO: 15]

P—T—S—L—A—L—L.   [SEQ ID NO: 16]

The three peptides indicated with an asterisk showed some inhibitory effect on virus release in the above assay; whereas, the other peptides were inactive when tested at 1 mg/ml.

The inhibitory enhancement of the small peptides of the invention by acylation of the N-terminus is illustrated by octanoylation of the heptapeptide amide having the following amino acid sequence [SEQ ID NO:17]:

| OCTANOYLATED HEPTAPEPTIDE L-T-P-Y-A-L-A$^a$ | | | |
|---|---|---|---|
| Test | | Ratio of Extracellular Virus to Intracellular Virus Proteins | |
| 1. | Peptide | .10 | (60%)$^b$ |
|  | None | .25 | |
| 2. | Peptide | .27 | (50%) |
|  | None | .56 | |
| 3. | Peptide | .19 | (50%) |

TABLE II-continued
INHIBITION OF SINDBIS VIRUS RELEASE BY OCTANOYLATED HEPTAPEPTIDE L-T-P-Y-A-L-A[a]

| Test | Ratio of Extracellular Virus to Intracellular Virus Proteins |
|---|---|
| None | .36 |

[a]Peptide (0.1 mg/ml final level) was added 4 hr post infection with [$^{35}$S]methionine. Virus and cells were collected 2 hr. later.
[b]Degree of Inhibition.
Note:
1. There was no inhibition of intracellular virus protein synthesis by the peptide at this level.
2. There was no inhibition of vesicular stomatitis virus formation and secretion by this peptide at this level.

EXAMPLE 2

This example describes additional results of tests in which small peptides were used to inhibit the final steps in formation and release of enveloped RNA viruses from infected host cells. These viruses were influenza virus, vesicular stomatitis virus and Sindbis virus. See Dubois-Dalcq et al., *Assembly of Enveloped RNA Viruses*, Springer-Verlag, Wein, 1984, for current models of the final replication stages of these viruses.

Influenza virus assembles as its eight segmented nucleocapsids interact with a membrane-associated matrix protein and two transmembrane glycoproteins—noted as the neuraminidase and the hemagglutinin. The hemagglutinin is post translationally cleaved into two polypeptides—HA1 and HA2.

Vesicular stomatitis virus, or VSV, assembles when its single nucleocapsid interacts with a membrane-associated matrix protein and a single transmembrane glycoprotein called G.

Sindbis virus assembly does not require a matrix protein. Its icosahedral nucleocapsid interacts directly with two transmembrane glycoproteins, E1 and E2.

Thus, assembly of these virions requires virus specific protein-protein and protein-RNA interactions.

In this example, peptides with sequences that mimic viral protein sequences critical to assembly are shown to inhibit viral replication by competing with the intact protein for binding sites. The sites for specific glycoprotein-protein interactions are listed in Table III.

TABLE III
GLYCOPROTEIN-PROTEIN INTERACTIONS SUSCEPTIBLE TO INHIBITION BY POLYPEPTIDES

| Virus | Protein |
|---|---|
| Influenza | Glycoprotein HA2-Matrix protein |
| Vesicular stomatitis | Glycoprotein G-Matrix protein |
| Sindbis | Glycoprotein E2-Nucleocapsid |

Each of the viruses contains a transmembranal glycoprotein that has a small cytoplasmic domain—a set of sequences that extend into the cytoplasm of the infected cell. The cytoplasmic domain is thought to interact directly with the intracellular viral components, i.e. the matrix proteins for influenza virus and VSV and the nucleocapsid for Sindbis virus. The glycoproteins targeted for these tests are the HA2 of the influenza virus, the G protein of vesicular stomatitis virus and the E2 protein of Sindbis virus.

Peptides with sequences identical to portions of the cytoplasmic domain of each of these glycoproteins were synthesized and purified by conventional solid phase procedures. Their structures were confirmed by mass spectroscopy and analysis of their sequence or composition. The assay used herein to test for their ability to inhibit virus release during a single replication cycle is outlined in Table IV. Chicken embryo fibroblasts (CEF) are infected with virus at a multiplicity of infection of 5. Four hours later peptide is added to the medium. After a half hour incubation, radioactive methionine is added and the system is labeled for 1.5 h. The extracellular virus is collected from the medium and the cells are harvested. Both fractions are subjected to SDS gel electrophoresis and the amount of virus released is measured by quantitating the amount of radioactivity in virus specific bands.

TABLE IV
ASSAY FOR INHIBITION OF VIRUS RELEASE BY PEPTIDES

| TIME (h) | ASSAY STEP |
|---|---|
| 0 | infect chicken embryo fibroblasts with virus at moi = 5 |
| 4 | add peptide to medium* |
| 4.5 | add [$^{35}$S]-methionine |
| 6 | collect virus from extracellular fluid (centrifugation or adsorption to polyanoic matrix-Cellufine sulfate from Amicon) harvest cells separate labeled virus proteins by SDS-PAGE quantitate by fluorography and scintillation counting of virus specific proteins |

*peptides insoluble in medium were first dissolved in either cetyl trimethylammonium bromide or dimethyl sulfoxide.

The detailed procedures for the synthesis and testing of the peptide, N-G-S-L-Q-C-R-I-C-I-NH$_2$ [SEQ ID NO:3], and the influenza virus inhibitory results are as follows:

A ten amino acid peptide whose sequence, N-G-S-L-Q-C-R-I-C-I-NH$_2$ [SEQ ID NO:3], corresponded to residues 213–222 at the carboxy terminus of the HA2 of A/WSN strain of influenza virus [Hiti et al., *Virology* 111, 113–124 (1981)]was synthesized as a carboxyamidated peptide by standard solid-phase techniques using t-butyloxy-carbonyl chemistry and purified by reverse phase HPLC. Its composition was verified by amino acid analysis and mass spectrometry. This aqueous-insoluble peptide was solubilized by adding a minimum volume of 27 µM cetyltrimethylammonium bromide (CTAB) and diluting with a phosphate-buffered saline solution. Varying concentrations were added to cultures of infected chicken embryo fibroblasts (CEF) at 4 h postinfection. Intracellular formation of virus-specific proteins and release of virions into the extracellular fluid were measured by labeling cells for 1.5 h with [$^{35}$S]-methionine 30 min after addition of the peptide and quantitating the levels of virus specific radiolabeled proteins after separation by SDS-PAGE. Virus released from cells was collected by adsorption to the anionic resin, Cellufine (Amicon). The recovery of radioactivity in virus-specific proteins after Cellufine adsorption was identical to that recovered by ultracentrifugation (1 h at 40,000 rpm, Beckman type 65 rotor). With the Cellufine procedure, it was found that some high molecular weight host-specific proteins secreted into the medium, possibly collagens (FIG. 2).

Results of these tests showed a dose-dependent inhibition of virus particle secretion with greater than a 90% block at 250 µg/ml (225 µM) and a half-maximal dose of less than 50 µg/ml (45 µM) (FIG. 1). Control samples containing the same amounts of detergent but no peptide did not affect the amount of virus released when added to cultures that received no peptide. A dose-dependent inhibiton of infectious influenza virions, measured by plaque titration of the cell-free medium, was similar to that found for particle release with a decrease from $3.8 \times 10^4$ to $1.4 \times 10^3$ pfu/ml at a dose of 200 μg/ml peptide (FIG. 1). In a second test where no radiolabel was included, a dose-dependent reduction in infectious virus titer was observed with a decrease in titer from $6.9 \times 10^4$ to $3.9 \times 10^4$ pfu/ml at a level of 200 μg/ml peptide (FIG. 1).

The inhibition of influenza virus release by peptide HA2 (213–222) was not caused by a general block in virus protein synthesis. No significant changes were detected in the synthesis of intracellular viral nucleoprotein and matrix protein in cells treated with increasing amounts of peptide (Table V). To determine if the inhibition of virus release was due to a decreased assembly of nucleocapsids, viral ribonucleoprotein particles (RNP) were isolated from cytoplasmic extracts of influenza virus-infected cells by centrifugation in glycerol gradients. WSN virus infected CEF, grown in 6-well cluster dishes and labeled with [$^{35}$S]-methionine as described in the procedure for FIG. 1, below, were collected and lysed with 0.2 ml 50 mM Tris, pH 7.5, 100 mM NaCl, 1 mM EDTA (TNE) containing 0.5% Triton X-100 nonionic detergent and 0.5% 1,5 napthalene disulfonic acid. The insoluble material was removed by centrifugation for 5 min in a microfuge at 4° C. The pellet was washed one time with 0.1 ml of the same buffer and the original supernatant and wash were combined. The extract was loaded onto a 30% to 70% glycerol gradient in TNE containing 0.05% Triton X-100, 0.05% 1,5 napthalene disulfonic acid and 5 μg/ml bovine serum albumin (BSA) and subjected to centrifugation in a SW41 swinging bucket rotor at 29,000 rpm for 16 h at 4° C. The gradients were fractionated and the proteins in the fractions analyzed by SDS-PAGE and fluorography. The amount of nucleoprotein in the RNP peak was quantitated by scintillation counting. The position of the viral RNP peak was identified in parallel tests that used [$^3$H]-uridine to label the RNA (0.1 mCi/-well of infected CEF) and by the sensitivity of the [$^{35}$S]methionine labeled nucleoprotein position in the gradient to RNase treatment (50 μg RNase for 45 min at 37° C.). The amount of nucleoprotein in the RNP peak from cells treated with 150 μg/ml peptide was 19% of the total cytoplasmic nucleoprotein compared to a value of 20% for samples that received no peptide. In this test, the peptide inhibited release of influenza virus particles by 70%.

Two types of tests showed that the inhibition of influenza virus particle release was highly specific for the peptide HA2 (213–222). First, the peptide was tested for its effect on two unrelated enveloped RNA viruses. At a concentration of 200 μg/ml, which inhibited the release of influenza virus by 90%, no block occurred in the release of Sindbis virus (FIG. 2). When tested at this same level with cells infected with vesicular stomatitis virus, the peptide blocked release by only 15%. Second, peptides equivalent in length and/or hydrophobicity but with different sequences failed to inhibit influenza virus release. Among these were two peptides that blocked release of Sindbis virus by greater than 50%: a hexapeptide, L-T-P-Y-A-L-amide [SEQ ID NO:7], and a nonapeptide, K-A-R-R-E-C-L-T-P [SEQ ID NO:10-](E2 (391–399), FIG. 2).

Initial tests have been performed to determine the precise specificity of peptide HA2 (213–222). The peptide described in the inhibitory tests, above, was prepared so that it had a C-terminal carboxyamide group; however, a peptide identical in sequence but with a free carboxy terminus was inactive in the assay. The carboxyamidated 8 amino acid peptide, N-G-S-L-Q-C-R-I [SEQ ID NO:18], which is identical in sequence to the inhibitory peptide but lacks the two amino acids at the carboxy terminus, also appeared to be non-inhibitory.

TABLE V

Effect of peptide on cellular protein synthesis

| Peptide Level (μg/ml) | Incorporation[a] (% of control) | |
|---|---|---|
| 0 (CTAB only)[b] | 117 +/−19 | (3)[c] |
| 20 | 110 +/−12 | (2) |
| 50 | 108 +/−12 | (2) |
| 100 | 94 +/−9 | (1) |
| 200 | 83 | (1) |
| 250 | 97 | (10) |

[a]Values were calculated from the amount of radioactivity incorporated into the viral nucleoprotein and matrix protein in CEF treated with the peptide HA2 (213-222) at the given concentrations, as described in the procedure for FIG. 1, below, compared to control cultures that received no peptide. The amount of radioactivity in the nucleoprotein and matrix protein in control cultures was $1.36 \times 10^6$ cpm (+/−23%, n = 4).
[b]The concentration of CTAB was 0.06 μg/ml.
[c]The number of tests is given in parentheses.

The following detailed procedures were carried out for obtaining the results shown in FIGS. 1 and 2.

FIG. 1. Dose-dependent inhibition of influenza virus formation by the HA2 peptide, N-G-S-L-Q-C-R-I-C-I-$NH_2$ [SEQ ID NO:3.

Secondary cultures of chicken embryo fibroblasts grown in Earle's minimal essential medium with 3% fetal bovine serum (FBS) in 6-well tissue culture dishes were infected with the A/WSN/33 strain of influenza virus at a multiplicity of infection of 5. Virus was added to cells in 0.2 ml of a phosphate-buffered saline solution containing 1% FBS and 1 h later 2 ml of complete medium was added. This medium was replaced 3 h later with medium lacking L-methionine and containing various amounts of peptide. Solutions of the peptide were prepared by adding 4–6 μl of 0.001% cetyltrimethylammonium bromide (CTAB) to 0.4–0.6 mg of peptide followed by 100–200 μl of phosphate buffered saline. These levels of detergent were not inhibitory to cell growth or virus replication based on results of control cell cultures that received equivalent amounts of CTAB alone (see Table 4). Samples of solubilized peptide were added to the cell medium to give peptide concentrations that ranged from 10 to 225 μM. The peptide solution was mixed immediately prior to adding it to the culture medium. After 0.5 h [$^{35}$S]-L-methionine (Amersham, 1500 Ci/mmol) was added to each well to a final concentration of 10 μCi/ml and an equivalent amount added 0.75 h later. After another 0.75 h the culture fluid was collected and the cell monolayers washed three times with 1 ml of cold phosphate-buffered saline. The washes were combined with the culture fluid and centrifuged briefly at 2000 rpm to remove any cellular debris. A 0.4 ml solution of Cellufine (Amicon), 10% v/v in phosphate buffered saline, was added to the combined washes and culture fluid and incubated at 23° for 1 h. Influenza virus was quantitatively bound to this resin under the conditions described. The Cellufine was pelleted by brief centrifugation, washed with phosphate buffered saline once and the bound virus proteins released by boiling in SDS-gel sample buffer [Laemmli, *Nature* 227, 680–685 (1970)]. The washed cell monolayer was scraped with cold phosphate buffered saline, cells collected by centrifugation and extracts prepared by adding SDS gel sample buffer. Virus proteins from the cells and the extracellular virus were separated by SDS-PAGE employing 11% acrylamide gels and the gels treated for fluorography [Bonner and Laskey, *Eur. J. Biochem.* 46, 83-88 (1974)]. Protein bands corresponding to the matrix and nucleoprotein were identified by fluorography, excised from the dried gel and radioactivity measured by liquid scintillation counting. The data from three tests are given (— —, — —, — —). For plaque titration of infectious virus, Madin Darby bovine kidney cells were grown to confluency in six well plates and influenza virus added in phosphate buffered saline containing 1% FBS. Monolayers were overlaid with Earle's minimal essential medium containing 1% agar and supplemented with basal medium Eagle's vitamins and amino acids, 2% FBS, 0.6% Hepes, pH 7.4, 30 μg/ml DEAE dextran, penicillin, streptomycin and mycostatin. Plaques were visualized with crystal violet after three days growth at 37° C. The data for two tests are given (—— ——, ——Δ——).

Figure 2:
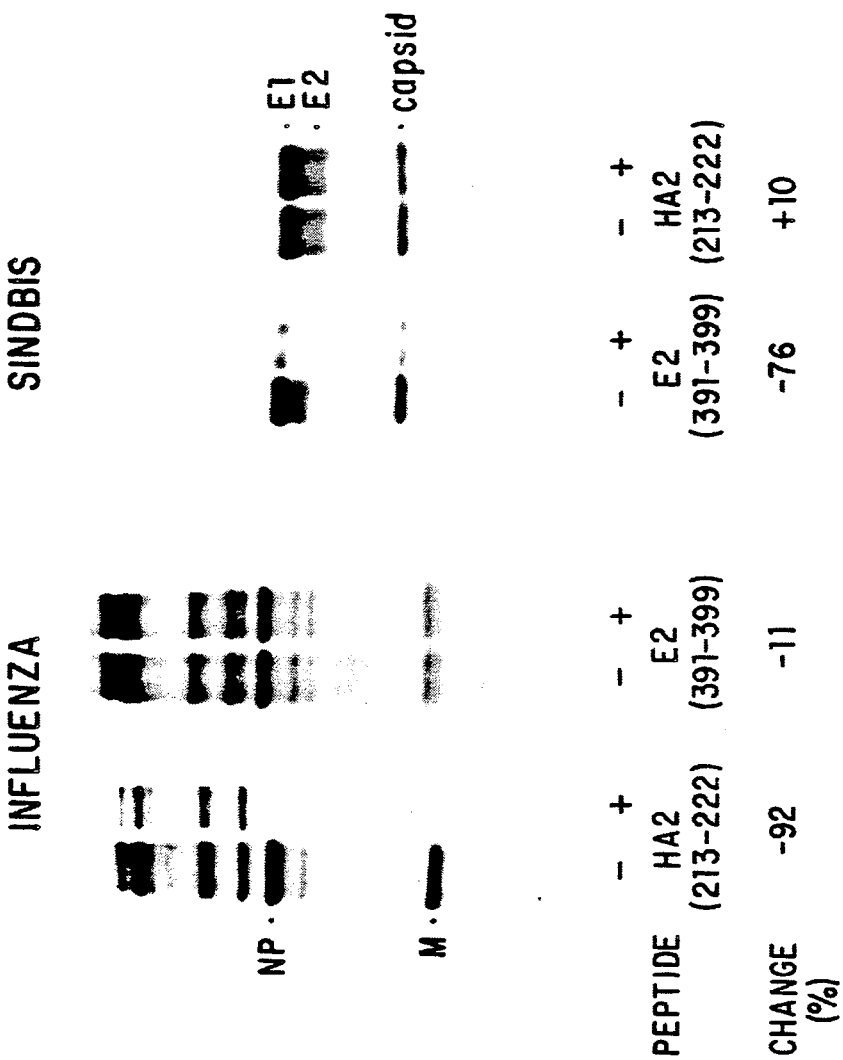
FIG. 2 shows the specificity of peptide inhibition in which radiolabeled cells infected with either influenza (left panel) or Sindbis virus (right panel) were treated either with the peptide HA2 (213–222) of FIG. 1 at 200 mg/ml or the peptide E2 (391–399) with the sequence KARRECLTP [SEQ ID NO:5] at 1 mg/ml.
Figure 3:
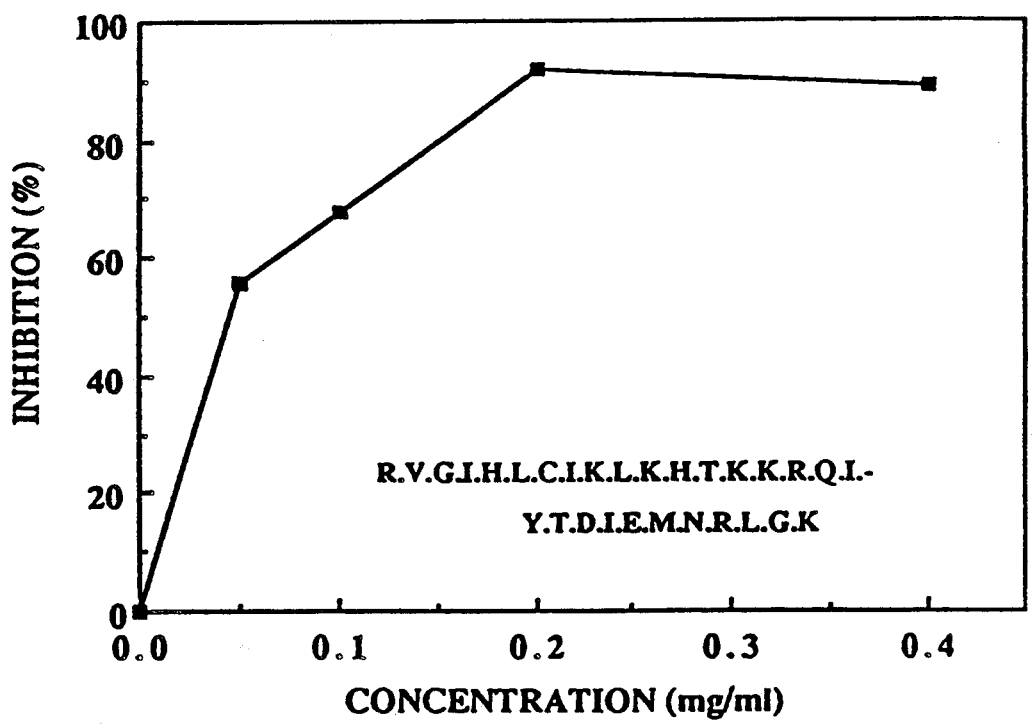
FIG. 3 is a graphical representation which shows the dose-dependent inhibition of vesicular stomatitis virus formation by the peptide, RVGIHLCIKLKHTKK-RQIYTDIEMNRLGK [SEQ ID NO:4], which is identical to amino acids 483–511 of the G protein of VSV (Indiana).

FIG. 2. Specificity of peptide inhibition. Cells infected with either influenza virus (left panel) or Sindbis virus (right panel) were treated with either the peptide HA2 (213-222) at 200 μg/ml or the peptide E2 (391-399) with sequence K-A-R-R-E-C-L-T-P [SEQ ID NO:5]at 1 mg/ml and radiolabeled as described in the procedure for FIG. 1, above. Virus released between 4 and 6 h postinfection was bound to Cellufine. Virion proteins were separated by SDS-PAGE and fluorographed. The virus specific proteins (nucleoprotein, NP, and matrix protein, M, for influenza virus and E1, E2, capsid for Sindbis virus) are indicated; the carets (>) indicate cellular proteins that bound to the Cellufine. The change in the amount of virions released compared to control cultures that received no peptide is given.

Amino acids are shown herein by standard one letter or three letter abbreviations as follows:

| Abbreviated Designation | | Amino Acid |
| --- | --- | --- |
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Various other examples will be apparent to the person skilled in the art after reading the present disclosure without departing from the spirit and scope of the invention. It is intended that all such other examples be included within the scope of the appended claims.

What is claimed is:

1. An antiviral peptide having the amino acid sequence N-G-S-L-Q-C-R-I-C-I-NH$_2$ [SEQ ID NO:3].

2. The method of inhibiting viral intracellular replication of influenza comprising subjecting said virus to an inhibitory effective amount of a peptide of claim 1.

* * * * *

SEQUENCE LISTING (1) GENERAL INFORMATION:

(i) APPLICANT: Schlesinger, Milton J.

Collier, Nancy C.

Adams, Steven P.

(ii) TITLE OF INVENTION: Antiviral Peptides (iii) NUMBER OF SEQUENCES: 18

(iv) CORRESPONDENCE ADDRESS:

(A) ADDRESSEE: Scott J. Meyer, Monsanto Co. A3SD (B) STREET: 800 N. Lindbergh Blvd.

(C) CITY: St. Louis (D) STATE: MO (E) COUNTRY: USA (F) ZIP: 63167

(v) COMPUTER READABLE FORM:

(A) MEDIUM TYPE: Floppy disk (B) COMPUTER: IBM PC compatible (C) OPERATING SYSTEM: PC-DOS/MS-DOS (D) SOFTWARE: PatentIn Release #1.0, Version #1.25

(vi) CURRENT APPLICATION DATA:

(A) APPLICATION NUMBER:

(B) FILING DATE:

(C) CLASSIFICATION:

(vii) PRIOR APPLICATION DATA:

(A) APPLICATION NUMBER: US 07/305,148

(B) FILING DATE: 01-FEB-1989

(viii) ATTORNEY/AGENT INFORMATION:

(A) NAME: Meyer, Scott J.

(B) REGISTRATION NUMBER: 25275

(C) REFERENCE/DOCKET NUMBER: 07-24(696)A (ix) TELECOMMUNICATION INFORMATION:

(A) TELEPHONE: (314)694-3117

(2) INFORMATION FOR SEQ ID NO:1:

(i) SEQUENCE CHARACTERISTICS:

(A) LENGTH: 6 amino acids (B) TYPE: amino acid (C) STRANDEDNESS: single (D) TOPOLOGY: linear (ii) MOLECULE TYPE: peptide (xi) SEQUENCE DESCRIPTION: SEQ ID NO:1:

Leu Thr Pro Tyr Ala Leu
1               5

(2) INFORMATION FOR SEQ ID NO:2:

(i) SEQUENCE CHARACTERISTICS:

(A) LENGTH: 7 amino acids (B) TYPE: amino acid (C) STRANDEDNESS: single (D) TOPOLOGY: linear (ii) MOLECULE TYPE: peptide (xi) SEQUENCE DESCRIPTION: SEQ ID NO:2:

Leu Thr Pro Tyr Ala Leu Ala
1               5

(2) INFORMATION FOR SEQ ID NO:3:

(i) SEQUENCE CHARACTERISTICS:

(A) LENGTH: 10 amino acids (B) TYPE: amino acid (C) STRANDEDNESS: single (D) TOPOLOGY: linear (ii) MOLECULE TYPE: peptide (ix) FEATURE:

(A) NAME/KEY: Modified-site (B) LOCATION: 10

(D) OTHER INFORMATION: /label= amide (xi) SEQUENCE DESCRIPTION: SEQ ID NO:3:

Asn Gly Ser Leu Gln Cys Arg Ile Cys Ile
1             5                    10

(2) INFORMATION FOR SEQ ID NO:4:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Arg Val Gly Ile His Leu Cys Ile Lys Leu Lys His Thr Lys Lys Arg
    1               5                   10                  15

Gln Ile Tyr Thr Asp Ile Glu Met Asn Arg Leu Gly Lys
                20                  25

(2) INFORMATION FOR SEQ ID NO:5:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Lys Ala Arg Arg Glu Cys Leu Thr Pro
    1               5

(2) INFORMATION FOR SEQ ID NO:6:

(i) SEQUENCE CHARACTERISTICS:
       (A) LENGTH: 33 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:6:

Lys Ala Arg Arg Glu Cys Leu Thr Pro Tyr Ala Leu Ala Pro Asn Ala
   1               5                   10                  15

Val Ile Pro Thr Ser Leu Ala Leu Leu Cys Cys Val Arg Ser Ala Asn
                   20                  25                  30

Ala (2) INFORMATION FOR SEQ ID NO:7:

(i) SEQUENCE CHARACTERISTICS:
       (A) LENGTH: 6 amino acids
       (B) TYPE: amino acid
       (C) STRANDEDNESS: single
       (D) TOPOLOGY: linear (ii) MOLECULE TYPE: peptide (ix) FEATURE:

(A) NAME/KEY: Modified-site (B) LOCATION: 6

(D) OTHER INFORMATION: /label= amide (xi) SEQUENCE DESCRIPTION: SEQ ID NO:7:

Leu Thr Pro Tyr Ala Leu
1              5

(2) INFORMATION FOR SEQ ID NO:8:

(i) SEQUENCE CHARACTERISTICS:

(A) LENGTH: 23 amino acids (B) TYPE: amino acid (C) STRANDEDNESS: single (D) TOPOLOGY: linear (ii) MOLECULE TYPE: peptide (ix) FEATURE:

(A) NAME/KEY: Modified-site (B) LOCATION: 23

(D) OTHER INFORMATION: /label= amide (xi) SEQUENCE DESCRIPTION: SEQ ID NO:8:

Lys Ala Arg Arg Glu Cys Leu Thr Pro Tyr Ala Leu Ala Pro Asn Ala
1              5              10              15

Val Ile Pro Thr Ser Leu Ala
         20

(2) INFORMATION FOR SEQ ID NO:9:

(i) SEQUENCE CHARACTERISTICS:

(A) LENGTH: 20 amino acids (B) TYPE: amino acid (C) STRANDEDNESS: single (D) TOPOLOGY: linear (ii) MOLECULE TYPE: peptide (ix) FEATURE:

(A) NAME/KEY: Modified-site (B) LOCATION: 20

(D) OTHER INFORMATION: /label= amide (xi) SEQUENCE DESCRIPTION: SEQ ID NO:9:

Arg Glu Cys Leu Thr Pro Tyr Ala Leu Ala Pro Asn Ala Val Ile Pro
1               5                  10                  15

Thr Ser Leu Ala
        20

(2) INFORMATION FOR SEQ ID NO:10:

(i) SEQUENCE CHARACTERISTICS:

(A) LENGTH: 9 amino acids (B) TYPE: amino acid (C) STRANDEDNESS: single (D) TOPOLOGY: linear (ii) MOLECULE TYPE: peptide (ix) FEATURE:

(A) NAME/KEY: Modified-site (B) LOCATION: 9

(D) OTHER INFORMATION: /label= amide (xi) SEQUENCE DESCRIPTION: SEQ ID NO:10:

Lys Ala Arg Arg Glu Cys Leu Thr Pro
    1               5

(2) INFORMATION FOR SEQ ID NO:11:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 6
        (D) OTHER INFORMATION: /label= amide (xi) SEQUENCE DESCRIPTION: SEQ ID NO:11:

Lys Ala Arg Arg Glu Cys
    1               5

(2) INFORMATION FOR SEQ ID NO:12:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
    (A) NAME/KEY: Modified-site
    (B) LOCATION: 6
    (D) OTHER INFORMATION: /label= amide (xi) SEQUENCE DESCRIPTION: SEQ ID NO:12:

Ala Leu Ala Pro Asn Ala
1               5

(2) INFORMATION FOR SEQ ID NO:13:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 6
        (D) OTHER INFORMATION: /label= amide (xi) SEQUENCE DESCRIPTION: SEQ ID NO:13:

Val Ile Pro Thr Ser Leu
1               5

(2) INFORMATION FOR SEQ ID NO:14:

(i) SEQUENCE CHARACTERISTICS:

(A) LENGTH: 16 amino acids (B) TYPE: amino acid (C) STRANDEDNESS: single (D) TOPOLOGY: linear (ii) MOLECULE TYPE: peptide (ix) FEATURE:

(A) NAME/KEY: Modified-site (B) LOCATION: 16

(D) OTHER INFORMATION: /label= amide (xi) SEQUENCE DESCRIPTION: SEQ ID NO:14:

Tyr Ala Leu Ala Pro Asn Ala Val Ile Pro Thr Ser Leu Ala Leu Leu 1                5                  10                      15

(2) INFORMATION FOR SEQ ID NO:15:

(i) SEQUENCE CHARACTERISTICS:

(A) LENGTH: 11 amino acids (B) TYPE: amino acid (C) STRANDEDNESS: single (D) TOPOLOGY: linear (ii) MOLECULE TYPE: peptide (ix) FEATURE:

(A) NAME/KEY: Modified-site (B) LOCATION: 11

(D) OTHER INFORMATION: /label= amide (xi) SEQUENCE DESCRIPTION: SEQ ID NO:15:

Asn Ala Val Ile Pro Thr Ser Leu Ala Leu Leu
1               5                   10

(2) INFORMATION FOR SEQ ID.NO:16:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 7
        (D) OTHER INFORMATION: /label= amide (xi) SEQUENCE DESCRIPTION: SEQ ID NO:16:

Pro Thr Ser Leu Ala Leu Leu
1               5

(2) INFORMATION FOR SEQ ID NO:17:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide
    (ix) FEATURE:
        (A) NAME/KEY: Modified-site (B) LOCATION: 1

(D) OTHER INFORMATION: /label= octanoyl (ix) FEATURE:

(A) NAME/KEY: Modified-site (B) LOCATION: 7

(D) OTHER INFORMATION: /label= amide (xi) SEQUENCE DESCRIPTION: SEQ ID NO:17:

Leu Thr Pro Tyr Ala Leu Ala
    1               5

(2) INFORMATION FOR SEQ ID NO:18:

(i) SEQUENCE CHARACTERISTICS:

(A) LENGTH: 8 amino acids (B) TYPE: amino acid (C) STRANDEDNESS: single (D) TOPOLOGY: linear (ii) MOLECULE TYPE: peptide (ix) FEATURE:

(A) NAME/KEY: Modified-site (B) LOCATION: 8

(D) OTHER INFORMATION: /label= amide (xi) SEQUENCE DESCRIPTION: SEQ ID NO:18:

Asn Gly Ser Leu Gln Cys Arg Ile
    1               5